(12) United States Patent
Kobayashi et al.

(10) Patent No.: US 7,964,556 B1
(45) Date of Patent: Jun. 21, 2011

(54) ANTIMICROBIAL PEPTIDES AND USE THEREOF

(75) Inventors: Nahoko Kobayashi, Nagoya (JP); Tetsuhiko Yoshida, Nagoya (JP)

(73) Assignee: Toagosei Co., Ltd, Tokyo (JP)

( * ) Notice: Subject to any disclaimer, the term of this patent is extended or adjusted under 35 U.S.C. 154(b) by 0 days.

(21) Appl. No.: 11/761,869

(22) Filed: Jun. 12, 2007

Related U.S. Application Data

(62) Division of application No. 11/294,583, filed on Dec. 5, 2005, now abandoned.

(30) Foreign Application Priority Data

Dec. 6, 2004 (JP) ................................. 2004-352385

(51) Int. Cl.
*A61K 38/00* (2006.01)
*A61K 38/04* (2006.01)
*A61K 51/00* (2006.01)

(52) U.S. Cl. ......... 514/1.1; 530/326; 530/327; 424/1.69

(58) Field of Classification Search .................... 514/2
See application file for complete search history.

(56) References Cited

U.S. PATENT DOCUMENTS

| | | | |
|---|---|---|---|
| 5,547,939 A | 8/1996 | Selsted | |
| 5,789,542 A | 8/1998 | McLaughlin et al. | |
| 5,807,746 A | 9/1998 | Lin et al. | |
| 5,877,282 A | 3/1999 | Nadler et al. | |
| 5,962,415 A | 10/1999 | Nadler | |
| 6,043,339 A | 3/2000 | Lin et al. | |
| 6,180,604 B1 | 1/2001 | Fraser et al. | |
| 6,191,254 B1 | 2/2001 | Falla et al. | |
| 6,303,575 B1 | 10/2001 | Selsted | |
| 6,476,189 B1 | 11/2002 | Yamakawa et al. | |
| 2002/0160952 A1* | 10/2002 | Kazantsev et al. | 514/12 |
| 2005/0171335 A1 | 8/2005 | Kourai et al. | |

FOREIGN PATENT DOCUMENTS

| | | |
|---|---|---|
| JP | 2001186887 | 7/2001 |
| JP | 2003-508788 | 3/2003 |
| JP | 2003-521499 | 7/2003 |
| WO | 9402610 | 2/1994 |
| WO | 9636692 | 11/1996 |
| WO | 9851794 | 11/1998 |
| WO | 9926971 | 6/1999 |
| WO | 9929721 | 6/1999 |
| WO | 9967284 | 12/1999 |
| WO | 0009553 | 2/2000 |
| WO | 0059527 | 10/2000 |
| WO | 0109175 | 2/2001 |
| WO | 0210201 | 2/2002 |
| WO | 03091429 | 11/2003 |

OTHER PUBLICATIONS

Beven et al, Effects on *mollicutes* (wall-less bacteria) of synthetic peptides comprising a signal peptide or a membrane fusion peptide, and a nuclear localization sequence (NLS) a comparison with melittin, Biochim Biophys Acta Oct. 23, 1997; 1329(2), pp. 357-369.

Chaloin et al, Ionic Channels formed by a primary amphipathic peptide containing a signal peptide and a nuclear localization sequence, Biochim Biophys Acta Oct. 15, 1998; 1375(1-2), pp. 52-60.

Yechiel, From innate immunity to de-novo designed antimicrobial peptides, Current Pharmaceutical Design, 2002, vol. 8, No. 9, Apr. 1, 2002, pp. 715-725.

Kubota et al, A cis-acting peptide signal in a human immunodeficiency virus type I Rev which inhibits nuclear entry of small proteins, Oncogene, vol. 16 (1998), pp. 1851-1861.

Fang et al, Trans-Dominant Negative HIV Type 1 Rev with Intact Domains of NLS/NOS and NES, AIDS Research and Human Retroviruses, vol. 18, No. 10 (2002), pp. 705-708.

Goode et al, Identification of a novel microtubule binding and assembly domain in the developmentally regulated inter-repeat region of tau, The Journal of Cell Biology, vol. 124 (1994), pp. 769-782.

Goode et al, Functional interactions between the proline-rich and repeat regions of tau enhance microtubule binding and assembly, Molecular Biology of the Cell, vol. 8 (1997), pp. 353-365.

Bergen et al, Assembly of tau protein into Alzheimer paired helical filaments depends on a local sequence motif forming structure, PNAS, vol. 97, No. 10 (2000), pp. 5129-5134.

Japanese Office Action for 2004-352385 mailed on Jul. 8, 2010.

* cited by examiner

*Primary Examiner* — Maury Audet
(74) *Attorney, Agent, or Firm* — Turocy & Watson, LLP

(57) ABSTRACT

Antimicrobial agent including an artificially synthesized antimicrobial peptide that does not occur naturally is provided by present invention. The peptide included in the antimicrobial agent includes 1 unit, 2 units or more units of sequence(s) or sequence(s) with partial modification, the sequence(s) composed of at least 6 contiguous amino acid residues selected from any one of amino acid sequences:

(a) KVQIINKK;
(b) SVQIVYKP;
(c) QVEVKSEK;
(d) KKVAVVRT;
(e) KKVAIIRT;
(f) KKPTSAK, and the total number of amino acid residues included in 1 unit, 2 units or more units of sequence(s) is 30% or more of the total number of amino acid residues constituting the peptide chain.

3 Claims, No Drawings

SEQUENCE LISTING

<160> NUMBER OF SEQ ID NOS: 39

<210> SEQ ID NO 1
<211> LENGTH: 8
<212> TYPE: PRT
<213> ORGANISM: Rattus norvegicus

<400> SEQUENCE: 1

Lys Val Gln Ile Ile Asn Lys Lys
1               5

<210> SEQ ID NO 2
<211> LENGTH: 8
<212> TYPE: PRT
<213> ORGANISM: Rattus norvegicus

<400> SEQUENCE: 2

Ser Val Gln Ile Val Tyr Lys Pro
1               5

<210> SEQ ID NO 3
<211> LENGTH: 8
<212> TYPE: PRT
<213> ORGANISM: Rattus norvegicus

<400> SEQUENCE: 3

Gln Val Glu Val Lys Ser Glu Lys
1               5

<210> SEQ ID NO 4
<211> LENGTH: 8
<212> TYPE: PRT
<213> ORGANISM: Rattus norvegicus

<400> SEQUENCE: 4

Lys Lys Val Ala Val Val Arg Thr
1               5

<210> SEQ ID NO 5
<211> LENGTH: 8
<212> TYPE: PRT
<213> ORGANISM: Mus musculus

<400> SEQUENCE: 5

Lys Lys Val Ala Ile Ile Arg Thr
1               5

```
<210> SEQ ID NO 6
<211> LENGTH: 7
<212> TYPE: PRT
<213> ORGANISM: Homo sapiens

<400> SEQUENCE: 6

Lys Lys Pro Thr Ser Ala Lys
1               5

<210> SEQ ID NO 7
<211> LENGTH: 7
<212> TYPE: PRT
<213> ORGANISM: Simian virus 40

<400> SEQUENCE: 7

Pro Lys Lys Lys Arg Lys Val
1               5

<210> SEQ ID NO 8
<211> LENGTH: 12
<212> TYPE: PRT
<213> ORGANISM: Human immunodeficiency virus

<400> SEQUENCE: 8

Arg Gln Ala Arg Arg Asn Arg Arg Arg Arg Trp Arg
1               5                   10

<210> SEQ ID NO 9
<211> LENGTH: 7
<212> TYPE: PRT
<213> ORGANISM: Mus musculus

<400> SEQUENCE: 9

Arg Ile Arg Lys Lys Leu Arg
1               5

<210> SEQ ID NO 10
<211> LENGTH: 9
<212> TYPE: PRT
<213> ORGANISM: Hepatitis C virus

<400> SEQUENCE: 10

Pro Pro Arg Lys Lys Arg Thr Val Val
1               5

<210> SEQ ID NO 11
<211> LENGTH: 9
<212> TYPE: PRT
<213> ORGANISM: Human immunodeficiency virus

<400> SEQUENCE: 11

Arg Lys Lys Arg Arg Gln Arg Arg Arg
1               5

<210> SEQ ID NO 12
<211> LENGTH: 5
<212> TYPE: PRT
<213> ORGANISM: Homo sapiens

<400> SEQUENCE: 12

Pro Arg Arg Arg Lys
1               5

<210> SEQ ID NO 13
<211> LENGTH: 7
<212> TYPE: PRT
```

<213> ORGANISM: avian neuroretina

<400> SEQUENCE: 13

Leu Lys Arg Lys Leu Gln Arg
1               5

<210> SEQ ID NO 14
<211> LENGTH: 6
<212> TYPE: PRT
<213> ORGANISM: Homo sapiens

<400> SEQUENCE: 14

Leu Met Trp Trp Met Leu
1               5

<210> SEQ ID NO 15
<211> LENGTH: 6
<212> TYPE: PRT
<213> ORGANISM: Drosophila melanogaster

<400> SEQUENCE: 15

Leu Met Trp Trp Leu Leu
1               5

<210> SEQ ID NO 16
<211> LENGTH: 6
<212> TYPE: PRT
<213> ORGANISM: Arabidopsis thaliana

<400> SEQUENCE: 16

Cys Leu Phe Trp Leu Leu
1               5

<210> SEQ ID NO 17
<211> LENGTH: 6
<212> TYPE: PRT
<213> ORGANISM: Saccharomyces cerevisiae

<400> SEQUENCE: 17

Leu Ile Trp Tyr Leu Leu
1               5

<210> SEQ ID NO 18
<211> LENGTH: 6
<212> TYPE: PRT
<213> ORGANISM: Haloarcula marismortui

<400> SEQUENCE: 18

Val Val Tyr Trp Leu Leu
1               5

<210> SEQ ID NO 19
<211> LENGTH: 6
<212> TYPE: PRT
<213> ORGANISM: Escherichia coli

<400> SEQUENCE: 19

Leu Tyr Leu Gly Ala Val
1               5

<210> SEQ ID NO 20
<211> LENGTH: 6
<212> TYPE: PRT
<213> ORGANISM: Pediococcus acidilactici

<400> SEQUENCE: 20

```
Leu Ile Thr Ser Lys Met
1               5
```

<210> SEQ ID NO 21
<211> LENGTH: 6
<212> TYPE: PRT
<213> ORGANISM: Acanthamoeba castellanii

<400> SEQUENCE: 21

```
Phe Phe Tyr Met Val Ile
1               5
```

<210> SEQ ID NO 22
<211> LENGTH: 6
<212> TYPE: PRT
<213> ORGANISM: Staphylococcus aureus

<400> SEQUENCE: 22

```
Leu Leu Thr Ala Lys Met
1               5
```

<210> SEQ ID NO 23
<211> LENGTH: 7
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 23

```
Lys Lys Val Ala Val Val Arg
1               5
```

<210> SEQ ID NO 24
<211> LENGTH: 8
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 24

```
Lys Val Gln Ile Ile Asn Lys Lys
1               5
```

<210> SEQ ID NO 25
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 25

```
Leu Lys Arg Lys Leu Gln Arg Val Gln Ile Val Tyr Lys
1               5                   10
```

<210> SEQ ID NO 26
<211> LENGTH: 13
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 26

```
Leu Lys Arg Lys Leu Gln Arg Val Gln Ile Ile Asn Lys
```

<210> SEQ ID NO 27
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 27

Lys Lys Val Ala Val Val Arg Lys Lys Val Ala Val Val Arg
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 28

Lys Val Gln Ile Ile Asn Lys Lys Lys Val Gln Ile Ile Asn Lys Lys
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 29

Arg Lys Lys Lys Arg Lys Val Lys Lys Val Ala Val Val Arg
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 30

Lys Lys Val Ala Val Val Arg Thr Lys Lys Val Ala Val Val Arg Thr
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 31

Arg Lys Lys Lys Arg Lys Val Lys Val Gln Ile Ile Asn Lys Lys
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Designed antimicrobial peptide containing a
      terminal amide group

```
<400> SEQUENCE: 32

Arg Lys Lys Lys Arg Lys Val Lys Val Ala Val Val Arg Thr
1               5                   10                  15

<210> SEQ ID NO 33
<211> LENGTH: 19
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 33

Lys Val Gln Ile Ile Asn Lys Lys Leu Asp Val Ser Asn Leu Met Trp
1               5                   10                  15

Trp Leu Leu

<210> SEQ ID NO 34
<211> LENGTH: 14
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 34

Lys Val Gln Ile Ile Asn Lys Lys Leu Met Trp Trp Leu Leu
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 35

Pro Pro Arg Lys Lys Arg Thr Val Val Lys Val Gln Ile Ile Asn Lys
1               5                   10                  15

Lys

<210> SEQ ID NO 36
<211> LENGTH: 12
<212> TYPE: PRT
<213> ORGANISM: Artificial Sequence
<220> FEATURE:
<223> OTHER INFORMATION: Designed antimicrobial peptide containing a
      terminal amide group

<400> SEQUENCE: 36

Val Gln Ile Val Tyr Lys Val Gln Ile Val Tyr Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Designed peptide containing a terminal amide
      group

<400> SEQUENCE: 37

Leu Pro Pro Leu Glu Arg Leu Thr Leu Asp
1               5                   10
```

```
<210> SEQ ID NO 38
<211> LENGTH: 6
<212> TYPE: PRT
<213> ORGANISM: Artificial Sequence
<220> FEATURE:
<223> OTHER INFORMATION: Designed Tau associated amino acid sequence

<400> SEQUENCE: 38

Val Gln Ile Ile Asn Lys
1               5

<210> SEQ ID NO 39
<211> LENGTH: 6
<212> TYPE: PRT
<213> ORGANISM: Artificial Sequence
<220> FEATURE:
<223> OTHER INFORMATION: Designed Tau associated amino acid sequence

<400> SEQUENCE: 39

Val Gln Ile Val Tyr Lys
1               5
```

ANTIMICROBIAL PEPTIDES AND USE THEREOF

CROSS REFERENCES TO OTHER APPLICATIONS

This application claims the benefit of priority from and is a Division of application Ser. No. 11/294,583 filed on Dec. 5, 2005, which is based upon and claims Paris Convention priority to Japanese Application No. 2004-352385 filed on Dec. 6, 2004, the entire content of both of which are hereby incorporated by reference.

TECHNICAL FIELD

The present invention relates to oligopeptide or polypeptide having antimicrobial property (hereinafter, antimicrobial peptide) and comprising independent peptide chains in the form that does not occur naturally, and their utilization. More specifically, the present invention relates to antimicrobial agent (composition) having such antimicrobial peptide as the main component.

BACKGROUND ART

It is generally believed that antimicrobial peptide has a broad antimicrobial spectrum such that drug resistant bacterium hardly appears, and therefore antimicrobial peptide is expected to be used for the purpose of preventing and treating bacterial infectious diseases in human beings and animals or providing antimicrobial properties to products such as food. A large number of antimicrobial peptides have been isolated from various animals and plants to date.

For example, a variety of antimicrobial peptides are disclosed in Japanese Laid-Open Patent Publication No. 2000-63400, Japanese Laid-Open Patent Publication No. 2001-186887, International Publication No. WO98/51794, International Publication No. WO99/26971, International Publication No. WO00/09553, International Publication No. WO00/59527 and International Publication No. WO01/09175. In addition, artificially synthesized antimicrobial peptides, which are designed and created by utilizing known amino acid sequence of which relations with antimicrobial properties have never been discussed, are reported in International Publication No. WO03/91429.

SUMMARY

The present invention provides, without utilizing the developmental approach of antimicrobial agent including the conventional antimicrobial peptides described in the aforementioned publications, new antimicrobial peptides composed of artificially designed amino acid sequences that are different from peptides existing and functioning as antimicrobial peptides in nature, and polynucleotides encoding such peptides. The present invention also provides antimicrobial agents (pharmaceutical compositions) having such non-natural antimicrobial peptide as the main component.

The inventors of the present invention focused on the amino acid sequence of Tau protein (τ protein), which is a kind of microtubule (more specifically, tubulin)-associated proteins (MAPs). Please refer to the following references regarding Tau protein:

Bruce L. Goode and Stuart C. Feinstein, *The Journal of Cell Biology*, Vol. 124, pp. 769-782 (1994)

Bruce L. Goode, Paul E. Denis, Dulal Panda, Monte J. Radeke, Herb P. Miller, Leslie Wilson and Stuart C. Feinstein), *Molecular Biology of the Cell*, Vo. 8, pp. 353-365 (1997)

M. von Bergen, P. Friedhoff, J. Biernat, J. Heberle, E.-M. Mandelkow and E. Mandelkow), *P N A S*, Vol. 97(10), pp. 5129-5134 (2000).

The inventors discovered that a peptide including a part of an amino acid sequence, which is a region (domain or motif) in which the association between Tau protein or other MAPs and the microtubule (tubulin) occurs, possesses high antimicrobial property against microbe such as bacteria, thereby leading to the accomplishment of the present invention.

The few antimicrobial peptides described herein are artificially synthesized antimicrobial peptides that do not occur naturally and having an antimicrobial property against at least one kind of bacteria. Such antimicrobial peptides have an amino acid sequence that constitutes at least a part of the Tau protein or other MAPs and has 1 unit, or 2 or more units of a sequence composed of at least 6 contiguous amino acid residues selected from the amino acid sequence within the region in which the association between such proteins and the microtubule occurs, or a sequence composed of said sequence with partial modification (for example, a sequence in which one or plurality of amino acid residues within such sequence are substituted conservatively.) It is desirable that a total number of amino acid residues included in said 1 unit, or 2 or more units of amino acid sequences is 30% or more of a total number of amino acid residues constituting the peptide chain.

The several preferred antimicrobial peptides described herein are artificially synthesized antimicrobial peptides that do not occur naturally and have an antimicrobial property against at least one kind of bacteria. Each of these antimicrobial peptides includes 1 unit, 2 units or more units of sequence(s), or said sequence(s) with partial modification (for example, one or a plurality of amino acid residues in the sequence are substituted conservatively), composed of at least 6 contiguous amino acid residues selected from any one of the amino acid sequences:

(a) KVQIINKK (SEQ ID NO: 1);
(b) SVQIVYKP (SEQ ID NO: 2);
(c) QVEVKSEK (SEQ ID NO: 3);
(d) KKVAVVRT (SEQ ID NO: 4);
(e) KKVAIIRT (SEQ ID NO: 5);
(f) KKPTSAK (SEQ ID NO: 6).

Desirably, a total number of amino acid residues included in said 1 unit, 2 units or more units of sequence(s) is 30% or more of a total number of amino acid residues constituting the peptide chain of the antimicrobial peptide described herein.

With regard to the amino acid sequences presence in the domain in which association with the microtubule occurs, the inventors of the present invention identified, in views of relatively short peptide chain that can be artificially synthesized, several domains including amino acid sequences that can exhibit antimicrobial property. The above-described amino acid sequences shown in (a) to (f) are typical examples of such amino acid sequences.

The amino acid sequences of (a), (b) and (c) are sequences included in the three inter-repeat domains exist respectively among the four repeat domain (R1, R2, R3, R4 from the N-terminal) presence in the C-terminal of Tau protein. Specifically, the (a) amino acid sequence shown in SEQ ID NO: 1 is a sequence composed of 8 amino acid residues at the N-terminal of the inter-repeat domain (IR/R1-R2) that exists between R1 and R2. The (b) amino acid sequence shown in SEQ ID NO: 2 is a sequence composed of 8 amino acid residues at the N-terminal of the inter-repeat domain (IR/R2-

R3) that exists between R2 and R3. The (c) amino acid sequence shown in SEQ ID NO: 3 is a sequence composed of 8 amino acid residues at the N-terminal of the inter-repeat domain (IR/R3-R4) that exists between R3 and R4 (see the aforementioned Bruce et al. (1994)). The present invention provides antimicrobial peptides including 1 unit, 2 units or more units of sequence(s) composed of at least 6 contiguous amino acid residues selected from amino acid sequences included in such inter-repeat domains.

The (d) amino acid sequence shown in SEQ ID NO: 4 is a sequence that exists in the proline rich domain of Tau protein and is being considered as a sequence in which association with microtubule occurs. Specifically, it is a sequence composed of the 8 amino acid residues, from the lysine residue at position 215 to the threonine residue at position 222, in the Tau protein from a rat (see the aforementioned Bruce et al. (1997)). The (e) amino acid sequence shown in SEQ ID NO: 5 is a partial sequence of a microtubule associated protein "MAP2" from a mouse, and is composed of the 8 amino acid residues having the same relationship with the above-described (d) sequence (see the aforementioned Bruce et al. (1997)). Further, the (f) amino acid sequence shown in SEQ ID NO: 6 is a partial sequence of a microtubule associated protein "MAP4" from a human, and is composed of the 8 amino acid residues having the same relationship with the above-described (d) sequence (see the aforementioned Bruce et al. (1997)). The present invention provides antimicrobial peptides including 1 unit, 2 units or more units of sequence(s) composed of at least 6 contiguous amino acid residues selected from specific amino acid sequences included in proline rich domain of Tau protein and amino acid sequences within other MAPs which are homologous with the specific sequences.

Therefore in another aspect, the present invention provides an antimicrobial agent (typically, compositions that can be used in the medical field and sanitary field) including, as a main component, an antimicrobial peptide having antimicrobial property against at least one kind of bacteria, said antimicrobial peptide including 1 unit, 2 units or more units of sequence(s) or said sequence(s) with partial modification (for example, one or a plurality of amino acid residues in the sequence are substituted conservatively), said sequence(s) composed of at least 6 contiguous amino acid residues selected from any one of the amino acid sequences (a) to (f), where a total number of amino acid residues included in said 1 unit, 2 units or more units of sequence(s) is 30% or more of a total number of amino acid residues constituting the peptide chain. The antimicrobial agent described herein typically includes at least one antimicrobial peptide and one carrier that can be pharmaceutically acceptable.

Since the antimicrobial agent provided by the present invention includes an antimicrobial peptide including a sequence, or said sequence with partial modification (hereinafter, Tau associated sequence), composed of at least 6 contiguous amino acid residues described herein, high antimicrobial activity against at least one kind of bacteria (gram-negative bacteria and/or gram-positive bacteria) or fungi can be exhibited.

Several desirable antimicrobial peptides described herein are artificially synthesized antimicrobial peptides that do not occur naturally and have an antimicrobial property against at least one kind of bacteria. Each of said antimicrobial peptides includes 2 or more units of sequences or said sequences with partial modification (for example, one or a plurality of amino acid residues in the sequence are substituted conservatively) arranged in proximity with each other, said sequences composed of at least 6 contiguous amino acid residues selected from any one of the amino acid sequences (a) to (f), and a total number of amino acid residues included in said 2 or more units of sequences is 30% or more of a total number of amino acid residues constituting the peptide chain. Antimicrobial peptides in which 2 or more units of such Tau associated sequences exist and are linked in tandem are particularly desirable.

The antimicrobial peptides having such structure can exhibit particularly high antimicrobial activity against at least one kind of bacteria (gram-negative bacteria and/or gram-positive bacteria) or fungi.

Therefore in another aspect, the present invention provides an antimicrobial agent including such antimicrobial peptides in which 2 or more units of Tau associated sequences are arranged in proximity with each other (desirably, in tandem).

Further, several other desirable antimicrobial peptides described herein are artificially synthesized antimicrobial peptides that do not occur naturally and have an antimicrobial property against at least one kind of bacteria. The antimicrobial peptides include 1 unit, 2 units or more units of sequence(s) or said sequence(s) with partial modification (for example, one or a plurality of amino acid residues in the sequence are substituted with the same kind of amino acid residues), said sequence(s) composed of at least 6 contiguous amino acid residues selected from any one of the amino acid sequences (a) to (f), and a total number of amino acid residues included in said 1 unit, 2 units or more units of sequence(s) is 30% or more of a total number of amino acid residues constituting the peptide chain. The antimicrobial peptides further include an amino acid sequence constituting nuclear localization signal sequence (NLS) or said amino acid sequence with partial modification.

Normally, nuclear localization signal sequences (NLSs) isolated from various organisms and viruses are partial sequences presence in various polypeptides transported to the nuclear within cells. The inventors of the present invention had discovered earlier that independent form of NLS itself possesses antimicrobial activity against bacteria and the like (see International Publication WO03/91429). Since the antimicrobial peptide having the above-described structure includes, as main components, an amino acid sequence constituting nuclear localization signal sequence (NLS) or said amino acid sequence with partial modification (hereinafter "NLS associated sequence") and the Tau associated sequence, the antimicrobial peptide can possess a particularly high antimicrobial activity. In addition, the antimicrobial peptide can also have a broad antimicrobial spectrum against gram-negative bacteria and/or gram-positive bacteria.

Therefore in another aspect, the present invention provides an antimicrobial agent including such antimicrobial peptides in which 1 unit, 2 units or more units of Tau associated sequences and NLS associated sequences are included.

Several other desirable antimicrobial peptides described herein are artificially synthesized antimicrobial peptides that do not occur naturally and have an antimicrobial property against at least one kind of bacteria. The antimicrobial peptides include 1 unit, 2 units or more units of sequence(s) or said sequence(s) with partial modification (for example, one or a plurality of amino acid residues in the sequence are substituted conservatively), said sequence(s) composed of at least 6 contiguous amino acid residues selected from any one of the amino acid sequences (a) to (f), and a total number of amino acid residues included in said 1 unit, 2 units or more units of sequence(s) is 30% or more of a total number of amino acid residues constituting the peptide chain. The antimicrobial peptides further include a sequence, or said sequence with partial modification, composed of at least 6 contiguous amino acid residues selected from an amino acid sequence constituting laminin binding site (LBS).

The inventors of the present invention discovered that peptide chain designed by combining the Tau associated sequence and a part of the amino acid sequence from a part known as laminin binding site (LBS) found in proteins that functions as receptors for laminin, which is non-collagen glycoprotein, can exhibits high antimicrobial activity against various microbes. Here, unless otherwise specified, "laminin binding site" is a term encompassing the general amino acid sequence known as amino acid sequence constituting the laminin binding site of laminin receptor, and is not limited to specific organism origin or specific amino acid sequence. Since the antimicrobial peptide having the above-described structure includes, as main components, a sequence, or said sequence with partial modification (hereinafter "LBS associated sequence"), composed of at least 6 contiguous amino acid residues selected from an amino acid sequence constituting laminin binding site (LBS) (specifically, amino acid sequence known for constituting LBS), the antimicrobial peptide can exhibit high antimicrobial activity against at least one kind of bacteria (gram-negative bacteria and/or gram-positive bacteria) or fungi.

Therefore in another aspect, the present invention provides an antimicrobial agent including such antimicrobial peptides in which 1 unit, 2 units or more units of Tau associated sequences and LB S associated sequences are included.

The antimicrobial peptide described herein is particularly desirable when a total number of amino acid residues constituting the peptide chain of said antimicrobial peptide is 30 or less (more desirably 20 or less). Peptides with such short chain can be easily chemically synthesized, and peptides having desirable capabilities can be easily provided. As a preferred embodiment of the antimicrobial peptide having the above-described structure, an antimicrobial peptide including an amino acid sequence, or said amino acid sequence with partial modification (for example, one or a plurality of amino acid residues in the sequence are substituted conservatively), selected from the group consisting of SEQ ID NO: 25 to SEQ ID NO: 36 as described below, and where a total number of amino acid residues constituting the peptide chain of said antimicrobial peptide is 30 or less, is described.

Antimicrobial peptides including such sequences (typically peptides composed of such sequences) can exhibit high antimicrobial activity against bacteria, particularly gram-positive bacteria such as *Staphylococcus aureus*.

Therefore, the present invention provides an antimicrobial agent including such antimicrobial peptides in which 1 unit, 2 units or more units of Tau associated sequences are included, and the total number of amino acid residues is 30 or less. For example, an antimicrobial agent including an antimicrobial peptide (for example a peptide composed only of amino acid sequence selected from the group consisting SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36) having an amino acid sequence, or said amino acid sequence with partial modification, selected from the group consisting of SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, and where the total number of amino acid residues constituting the peptide chain of the antimicrobial peptide is 30 or less is provided preferably.

As a peptide to be included in the antimicrobial agent, it is desirable that at least one of the amino acid residues is amidated. The stability (for example, protease resistance) of the structure of the antimicrobial peptide can be improved by amidating the carboxyl group of the amino acid residues (typically, amino acid residues at the C-terminal of the peptide chain).

The present invention also provides a method for producing an antimicrobial peptide that does not occur naturally and has an antimicrobial property against at least one kind of bacteria.

Specifically, one of the methods provided by the present invention for producing an antimicrobial peptide includes, (1) determining a sequence and/or said sequence with partial modification (for example, one or a plurality of amino acid residues in the sequence are substituted conservatively), said sequence composed of at least 6 contiguous amino acid residues selected from any one of the above-described amino acid sequences (a) to (f), (2) arranging said determined sequence and/or said determined sequence with partial modification in 2 or more units in proximity with each other, and designing the peptide chain such that a total number of amino acid residues included in said 2 or more units of sequences is 30% or more of a total number of amino acid residues constituting the peptide chain; and (3) synthesizing said designed peptide chain. More specifically, it is desirable that in (2), the peptide chain is designed such that said 2 or more units of sequences are linked in tandem. It is also desirable that the peptide chain is designed such that a total number of amino acid residues constituting the peptide chain is 30 or less.

Further, another one of the methods provided by the present invention for producing an antimicrobial peptide includes, (1) determining a sequence and/or said sequence with partial modification (for example, one or a plurality of amino acid residues in the sequence are substituted conservatively), said sequence composed of at least 6 contiguous amino acid residues selected from any one of the above-described amino acid sequences (a) to (f), (2) designing the peptide chain such that said determined sequence and/or said determined sequence with partial modification include(s) 1 unit, 2 units or more units, a total number of amino acid residues included in said 1 unit, 2 units or more units of amino acid sequences is 30% or more of a total number of amino acid residues, and the peptide chain further includes an amino acid sequence constituting nuclear localization signal sequence (NLS) or said amino acid sequence with partial modification, and (3) synthesizing said designed peptide chain. The peptide chain can also be designed such that 2 or more units of NLS associated sequences are included therein. In addition, it is desirable that the peptide chain is designed such that a total number of amino acid residues constituting the peptide chain is 30 or less.

Another one of the methods provided by the present invention for producing an antimicrobial peptide includes, (1) determining a sequence and/or said sequence with partial modification (for example, one or a plurality of amino acid residues in the sequence are substituted conservatively), said sequence composed of at least 6 contiguous amino acid residues selected from any one of the above-described amino acid sequences (a) to (f), (2) designing the peptide chain such that said determined sequence and/or said determined sequence with partial modification include(s) 1 unit, 2 units or more units, a total number of amino acid residues included in said 1 unit, 2 units or more units of amino acid sequences is 30% or more of a total number of amino acid residues, and the peptide chain further includes a sequence, or said sequence with partial modification, composed of at least 6 contiguous amino acid residues selected from an amino acid sequence constituting laminin binding site (LBS), and (3) synthesizing said designed peptide chain. The peptide chain can also be designed such that 2 or more units of LB S associated sequences are included therein. In addition, it is desirable that the peptide chain is designed such that a total number of amino acid residues constituting the peptide chain is 30 or less.

The present invention also provides an artificially designed polynucleotide that does not occur naturally, and the polynucleotide includes a nucleotide sequence and/or a nucleotide sequence complementary to said nucleotide sequence (for example, a polynucleotide substantially composed of such sequences) that encode(s) any of the antimicrobial peptides described herein.

Here, a polynucleotide including a nucleotide sequence and/or a nucleotide sequence complementary to said nucleotide sequence that encode(s) any amino acid sequences (or a modified sequence composed of said sequence with partial modification) shown in SEQ ID NO: 1 to SEQ ID NO: 36 is described as a desirable polynucleotide (for example, a polynucleotide substantially composed of such nucleotide sequences). The polynucleotide encodes peptides in which a total number of amino acid residues constituting the peptide chain are 30 or less.

DETAILED DESCRIPTION

Hereinafter, preferred embodiments of the present invention will be described. The matters apart from those specifically mentioned in this specification (e.g., primary structure or chain length of antimicrobial peptide) are necessary for performing the present invention (for example, general matters related to peptide synthesis, polynucleotide synthesis, and preparation of antimicrobial agent (pharmaceutical composition) including peptide as a component), and can be considered as matters of design by those skilled in the art based on the conventional technology in the fields of organic chemistry, biochemistry, genetic engineering, protein engineering, molecular biology, pharmaceuticals, medicine, hygieiology and the like. The present invention can be performed based on the contents described in this specification and the common technical knowledge in the field. In the following description, according to circumstances, amino acids are also expressed in the single letter code (but 3 letters code in the sequence table) based on the IUPAC-IUB nomenclature for amino acids.

In this specification, "artificially synthesized antimicrobial peptide that does not occur naturally" refers to antimicrobial peptide whose peptide chain alone does not independently occur in nature, but peptide segment that is artificially produced by chemical synthesis or biosynthesis (i.e., produced based on genetic engineering). In this specification, "antimicrobial peptide" is a term referring to amino acid polymer having a plurality of peptide bonds displaying antimicrobial activity against at least one kind of bacteria, and is not limited by the number of the amino acid residue constituting the peptide chain. The antimicrobial peptide in this specification also includes oligopeptides having 10 and below amino acid residue(s) or polypeptides containing more than 10 amino acid residues.

In this specification, "amino acid residue" is a term encompassing N-terminal amino acid of peptide chain and C-terminal amino acid of peptide chain, unless otherwise specified. In this specification, with respect to specific amino acid sequences, "sequences formed with partial modification (modified amino acid sequences)" refers to amino acid sequences formed by substituting, removing or adding (inserting) one or a plurality of amino acid residue without loosing the antimicrobial property of the specific amino sequences. For example, sequences formed by the so-called conservative amino acid replacement in which one or a plurality of amino acid residues (typically 2 or 3) are conservatively substituted (for example, sequences in which basic amino acid residue is substituted by other basic amino acid residue), or sequences formed by adding one or plurality (generally 2 to three) of amino acid residues to specific amino acid sequences and the like are typical examples included in the "sequences formed with partial modification (modified amino acid sequences)" of this specification.

In this specification, "polynucleotide" is a general term referring to polymer (nucleic acid) in which a plurality of nucleotides are bound by phosphodiester bonds, and is not limited by the number of the nucleotides. The polynucleotide may include DNA fragments and RNA fragments having various lengths. In addition, "artificially designed polynucleotide that does not occur naturally" refers to polynucleotide whose nucleotide chain (total length) alone does not independently occur in nature, but is artificially chemically synthesized or biosynthesized (i.e., produced based on genetic engineering).

The antimicrobial peptide described in this specification is artificially designed peptide that does not occur naturally, and typically, relatively short polypeptides or oligopeptides having Tau associated sequence. The antimicrobial peptide in the present invention is a peptide in which 30% or more of all the amino acid residues constituting the peptide chain is composed of 1 unit or 2 or more units of Tau associated sequence. Regarding Tau associated sequence, 1 unit refers to one sequence portion (domain or motif) constituting the Tau associated sequence. Therefore, the case where a peptide chain is composed of 2 units of Tau associated sequence means that two sequences independently regarded as Tau associated sequences, regardless of whether they are the same type or different types, are present in the peptide chain. Peptides composed of 1 unit or 2 units of Tau associated sequence are typical embodiments of the antimicrobial peptides described herein, and preferably serve as antimicrobial peptides constituting the main component of an antimicrobial agent (please refer to the following embodiments).

There is no specific limitation to the ratio of the Tau associated sequence in the entire amino acid sequence (thus the percentage of the total number of amino acid residues constituting the peptide chain that is accounted by the number of amino acid residues constituting the Tau associated sequence) as long as the percentage of the Tau associated sequence is 30% or more of the entire amino acid sequence. However, in the case where NLS associated sequence or LBS associated sequence is not included, it is more desirably for the ratio to be 50% or more, or still more desirably to be 70% or more, or particularly desirably to be 80% or more. For example, a peptide composed of 2 units (or 3 or more units) of Tau associated sequence arranged in tandem is a particularly desirable example.

It is desirable for all the amino acid residues constituting the antimicrobial peptide to be L-amino acid, but a part or all of the amino acid residues may be substituted with D-amino acids as long as the antimicrobial activity is not lost.

The chain length (thus the total number of amino acid residues) of the antimicrobial peptide described herein can vary according to the length of the Tau associated sequence (or NLS associated sequence or LBS associated sequence), and therefore there is no particular limitation. However, it is appropriate for the total number of amino acid residues constituting the peptide to be 100 or less (typically 50 or less), and desirably to be 30 or less, or particularly desirably to be 20 or less. For example, antimicrobial peptide composed of 10 to 20 amino acid residues possesses high antimicrobial activity, and at the same time is easy to synthesize and utilize. There is no particular limitation regarding the conformation (three-dimensional structure) of the peptide, as long as the peptide is antimicrobial in the environment in which it is used, but linear or helical peptide is desirable in view of its difficulty in becoming an immunogen (antigen). Peptide having such a shape hardly constitutes epitope. In view of this, it is desirable for antimicrobial peptide applying to an antimicrobial agent to be linear and having a relatively low molecular weight (typically, the number of amino acid residues: 10 to 30; for example, the number of amino acid residues: 10 to 20).

With regard to the Tau associated sequence for designing the antimicrobial peptide, any of the amino acid sequence selected from the above-described (a) to (f) can be utilized, or any of the short amino acid sequence composed of at least 6 (more desirably, at least 7) contiguous amino acid residues selected from the above-described (a) to (f) can be utilized. It is desirable to utilize at least 6 (more desirably, at least 7) contiguous amino acid residues selected from (a) KVQI-INKK (SEQ ID NO: 1), (b) SVQIVYKP (SEQ ID NO: 2) and (d) KKVAVVRT (SEQ ID NO: 4). Alternatively, antimicrobial peptide (peptide chain) utilizing such amino acid sequences with slight modification (for example, substituting, removing or adding one or a plurality (typically 2 or 3) of amino acid residues) can be easily designed. An example of a preferred modified sequence is a sequence in which one or a plurality of amino acid residues is substituted conservatively.

When designing a peptide chain including 2, 3 or more units of Tau associated sequence, it is desirable to designed it in such a way that such 2, 3 or more units of Tau associated sequence are arranged in proximity with each other within the peptide chain. It is particularly desirable that the peptide chain is designed in such a way that such 2, 3 or more units of Tau associated sequence are linked with each other in tandem. In this case, it is desirable that the C-terminal amino acid of one linked Tau associated sequence is directly bound with the N-terminal amino acid of another Tau associated sequence (see embodiment described hereinafter). However, one to several amino acid residues serving as linkers can also be interposed between two linked Tau associated sequences (see embodiment described hereinafter).

A preferred antimicrobial peptide described herein includes an antimicrobial peptide including a Tau associated sequence (or a Tau associated sequence and a LBS associated sequence) and a NLS associated sequence.

Conventionally, any of the native NLS sequences found in each kind of organism or virus can be utilized without modification as a NLS associated sequence. NLS with a relatively low number of amino acid residues (for example, NLS with 15 or less amino acid residues) is desirable. NLS shown in SEQ ID NO: 7, SEQ ID NO: 8, SEQ ID NO: 9, SEQ ID NO: 10, SEQ ID NO: 11, SEQ ID NO: 12 and SEQ ID NO: 13, respectively, are identified as specific examples. A peptide including 1, 2 or more units of 1, 2 or more kinds of such NLS sequence serving as NLS associated sequence is desirable. When designing a peptide chain including 2, 3 or more NLS associated sequences, it can be designed it in such a way that such 2, 3 or more units of NLS associated sequence are arranged in proximity with each other within the peptide chain. It is desirable that the peptide chain is designed in such a way that such 2, 3 or more units of NLS associated sequence are linked with each other in tandem.

NLS having a high rate of content of basic amino acid residue is particularly desirable. For example, NLS in which 40% or more (more desirably, 50% or more) of the amino acid residue are basic amino acid residue (lysine and/or arginine) is preferred. Peptide including 1, 2 or more units of 1, 2 or more kinds of such NLS is desirable. Further, peptide chain can also be designed by utilizing any of the native NLS sequence with slight modification (for example, substituting, removing or adding one or a plurality (typically 2 or 3) of amino acid residues). An example of a preferred modified sequence is a sequence in which one or a plurality of amino acid residues is substituted conservatively. A modified sequence (NLS associated sequence) formed by substituting one or a plurality of (typically 2 or 3) of non-basic amino acid residues with basic amino acid residues is also preferred.

A preferred antimicrobial peptide includes an antimicrobial peptide including a Tau associated sequence (or a Tau associated sequence and a NLS associated sequence) and a LBS associated sequence.

Conventionally, a sequence composed of at least 6 contiguous amino acid residues selected from any of the native LBS, known as the sequence constituting the laminin binding site, found in each kind of organism (eukaryotic organism or prokaryotic organism) can be utilized without modification as a LBS associated sequence. LBS shown in SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21 and SEQ ID NO: 22, respectively, are identified as specific examples. A peptide including 1, 2 or more units of 1, 2 or more kinds of such LBS sequence serving as LBS associated sequence is desirable. When designing a peptide chain including 2, 3 or more LBS associated sequences, it can be designed it in such a way that such 2, 3 or more units of LBS associated sequence are arranged in proximity with each other within the peptide chain. It is desirable that the peptide chain is designed in such a way that such 2, 3 or more units of LBS associated sequence are linked with each other in tandem. Further, peptide chain can also be designed by utilizing any of the native LBS sequence with slight modification (for example, substituting, removing or adding one or a plurality (typically 2 or 3) of amino acid residues). An example of a preferred modified sequence is a sequence in which one or a plurality (for example 1 to 3) of amino acid residues is substituted by the same kind of amino acid residues.

The antimicrobial peptides described herein can include partial sequences that are not present in Tau associated sequence, NLS associated sequence or LBS associated sequence as long as the antimicrobial property is not lost. Although there is no specific limitation, sequences that can maintain the three-dimensional shape of Tau associated sequence, NLS associated sequence and LBS associated sequence in a peptide chain are desirable for such partial sequences. Desirable antimicrobial peptide described herein includes peptide in which total number of amino acid residues is 100 or less (particularly desirably 30 or less), and in which ratio of amino acid residues constituting 1, 2 or more units of Tau associated sequence, 1, 2 or more units of NLS associated sequence and/or 1, 2 or more units of LBS associated sequence is 70% or more of the entire amino acid residues, or more desirably 80% or more of the entire amino acid residues, constituting the peptide chain. Alternatively, antimicrobial peptide composed of such sequences and part of the linkers (desirably, composed of 1 to several amino acid residues) interposed between such sequences is also preferred. Each antimicrobial peptide composed of the sequence shown in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, respectively, is specific preferred example of the antimicrobial peptide described herein. However, preferred peptide is not limited to peptide composed of such amino acid sequences. For example, modified amino acid sequence made by substituting conservatively one or a plurality of amino acid residues in any amino acid sequence shown in SEQ ID NO: 25 to SEQ ID NO: 36 with homologous amino acids also serves as desirable antimicrobial peptide.

Among the antimicrobial peptides described herein, those having relatively short peptide chain can be easily produced easily according to a general chemosynthetic method. For example, either a conventionally known solid-phase synthetic method or liquid-phase synthetic method can be used. A solid-phase synthetic method using Boc (t-butyloxycarbonyl) or Fmoc (9-fluorenylmethoxycarbonyl) as a protective group for the amino group is preferable. For the antimicrobial peptides described herein, peptide chain having a desired amino acid sequence and a modified (e.g., C-terminal amidated) portion can be easily synthesized by a solid-phase synthetic method using a commercially available peptide synthesis apparatus (available from PerSeptive Biosystems, Applied Biosystems or the like).

Alternatively, the antimicrobial peptides can be synthesized biologically based on a genetic engineering approach. This approach is preferable in producing a polypeptide having a relatively long peptide chain. In other words, DNA of a nucleotide sequence (including ATG start codon) that encodes the amino acid sequence of a desired antimicrobial peptide is synthesized. A recombinant vector having a gene construction substance for expression including this DNA and various regulatory elements (including promoter, ribosome binding site, terminator, enhancer, various cis-elements for controlling the expression level) is constructed in accordance with the host cell. This recombinant vector is transduced into a predetermined host cell (e.g., yeast, insect cell, plant cell, animal (mammalian) cell) by a regular technique, and tissues or organisms including the host cell or the cell are cultured under predetermined conditions. Thus, a desired polypeptide can be expressed and produced in the cell. Then, a polypeptide is isolated from the host cell (from a medium when secreted) and purified, so that a desired antimicrobial peptide can be obtained. Regarding methods for constructing the recombinant vector and methods for transducing the constructed recombinant vector into the host cell, conventional methods in this field can be utilized, and since such methods are not specific features of the present invention, detail descriptions will be omitted.

For example, a fusion protein expression system can be utilized for efficient mass production in a host cell. In other words, a gene (DNA) encoding an amino acid sequence of a desired antimicrobial peptide is chemically synthesized, and the synthesized gene is introduced into a preferred site of a suitable vector for expression of a fusion protein (e.g., a vector for expression of GST (Glutathione S-transferase) fusion protein such as pET series provided by Novagen and pGEX series provided by Amersham Bioscience). Then, the host cell (typically *E. coli*) is transformed by the vector. The obtained transformant is cultured so that a desired fusion protein is prepared. Then, the protein is extracted and purified. Then, the obtained purified fusion protein is cleaved by a predetermined enzyme (protease) and the separated desired peptide fragment (designed antimicrobial peptide) is collected by an affinity chromatography or the like. The antimicrobial peptide of the present invention can be produced by using such a conventionally known system for expression of a fusion protein (e.g., GST/H is system provided by Amersham Bioscience can be utilized).

Alternatively, a template DNA for a cell-free protein synthesis system (i.e., synthesized gene fragment including a nucleotide sequence encoding an amino acid sequence of an antimicrobial peptide) is constructed, and various compounds (ATP, RNA polymerase, amino acids and the like) are used, so that a targeted polypeptide can be synthesized in vitro by using a so-called cell-free protein synthesis system. Regarding the cell-free protein synthesis system, for example, an article by Shimizu et al. (Shimizu et al., *Nature Biotechnology*, 19, 751-755 (2001)), an article of Madin et al. (Madin et al., *Proc. Natl. Acad. Sci. USA*, 97(2), 559-564 (2000)) can be referred to. At the time of filing the present application, a large number of enterprises have already been entrusted with production of polypeptide based on the technologies described in these articles (all their contents are incorporated in the present specification as reference), and kits for cell-free protein synthesis (e.g., PROTEIOS (trademark) Wheat germ cell-free protein synthesis kit available from TOYOBO Co., Ltd. in Japan) are commercially available. Therefore, once an amino acid sequence to be utilized is determined and a peptide chain is designed as described above, then a desired antimicrobial peptide can be easily produced by a cell-free protein synthesis system according to the amino acid sequence. For example, the antimicrobial peptide can be easily produced based on PURESYSTEM (registered trademark) of POST GENOME INSTITUTE CO. LTD. in Japan.

A polynucleotide of a single strand or a double strand including a nucleotide sequence encoding the antimicrobial peptide described herein and/or a nucleotide sequence complementary to said sequence can be produced (synthesized) by a conventionally known method. In other words, a nucleotide sequence corresponding to the amino acid sequence of the antimicrobial peptide can be easily determined and provided by selecting a codon corresponding to each amino acid residue constituting the designed amino acid sequence. Then, once the nucleotide sequence is determined, then a polynucleotide (single strand) corresponding to the desired nucleotide sequence can be easily obtained by utilizing a DNA synthesis machine or the like. Furthermore, a targeted double strand DNA can be obtained by using various enzymatic synthesis means (typically PCR), using the obtained single strand as a template.

The polynucleotide provided by the present invention may be in the form of DNA or RNA (mRNA or the like). The DNA can be provided in the form of a double strand or a single strand. When it is provided in the form of a single strand, it may be in the form of a code chain (sense chain) or may be non-code chain (anti-sense chain) that is complementary thereto. As described above, the polynucleotide provided by the present invention can be used as a material for constructing a recombinant gene (expression cassette) for producing an antimicrobial peptide in various host cells or cell-free protein synthesis systems.

According to the present invention, a polynucleotide including a nucleotide sequence encoding an antimicrobial peptide, which contains a novel amino acid sequence and/or a nucleotide sequence complementary to said sequence can be provided. For example, as shown in SEQ ID NO: 27 and SEQ ID NO: 28, a peptide composed of amino acid sequence including 2, 3 or more units of Tau associated sequence in tandem is provided by the present invention, and a polynucleotide including a nucleotide sequence encoding such peptide, and/or a nucleotide sequence complementary to said sequence (for example the polynucleotide encoding the antimicrobial peptide of SEQ ID NO: 27 and SEQ ID NO: 28) is provided.

For example, an artificially designed polynucleotide that does not occur naturally, encoding a peptide chain composed of 100 or less amino acid residues (desirably about 50 or less, more desirably about 30 or less, and particularly desirably about 20 or less) is provided. Such polynucleotide includes (or is substantially composed of) a nucleotide sequence encoding an amino acid sequence and/or a nucleotide sequence complementary to said sequence, while said amino acid sequence includes an amino acid sequence shown in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, or a modified sequence of such amino acid sequence in which one or a plurality of amino acid residue(s) (for example, 2 to 3) is/are substituted conservatively.

In addition, another artificially designed polynucleotide that does not occur naturally is also provided. Such artificially designed polynucleotide includes (or is substantially composed of) a nucleotide sequence encoding an amino acid sequence and/or a nucleotide sequence complementary to said nucleotide sequence, while said nucleotide sequence encodes an antimicrobial peptide substantially composed of an amino acid sequence shown in SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35 and SEQ ID NO: 36, or a modified sequence of such amino acid sequence in which one or a plurality of amino acid residue(s) (for example, 2 to 3) is/are substituted conservatively.

The antimicrobial peptide described herein has a high antimicrobial activity against at least one kind of bacteria, has a relatively broad antimicrobial spectrum, and can be used preferably as the main component of an antimicrobial agent. For example, it can be used for the purpose of treating bacterial infection, sanitizing an external injury, preventing eye diseases, cleaning an oral cavity (gargling), preventing decay of foods, retaining freshness, removing odor, bacteriocide or bacteriostat for the surface of furniture or sanitary equipment and the like.

The antimicrobial agent used for such purposes (i.e. pharmaceutical composition) can include, apart from the antimicrobial peptide, various carriers that can be pharmaceutically acceptable. Carriers that are generally used as diluent, excipient and the like in peptide medication are desirable. Typically, water or physiological buffering solution is used, but apart from this, various organic solvent such as alcoholic (for example, ethanol) aqueous solution of appropriate concentration, glycerol, non-drying oil such as olive oil can also be used. Alternatively, liposome can also be used. As for secondary component, various filling agents, fillers, binders, moisturizers, surfactants, excipients, pigments, fragrances or the like can be used, depending on the use or the form of the antimicrobial agent. For the main component of the composition, as long as the antimicrobial property is not lost, acid addition salt of the peptide produced by the addition reaction generally used non-organic acid or organic acid according to conventional procedure can be used. Specific examples of acid that can formed such acid addition salt are non-organic acids such as hydrochloric acid, hydrobromic acid, sulfuric acid, phosphoric acid, or organic acids such as formic acid, acetic acid, propionic acid, glycolate acid, lactic acid, pyruvic acid, oxalic acid, succinic acid, maleic acid, malic acid, tartaric acid, citric acid, benzoic acid, salicylic acid, lower alkane sulfonic acid, benzenesulfonic acid, toluene sulfonic acid. Alternatively, not limited to the acid addition salt described above, other addition salt (for example metal salt) can also be used.

There is no particular limitation regarding the form of the antimicrobial agent. For example, examples of a typical form of medicines for internal or external use include ointment, liquid medicine, suspension, emulsion, aerosol, foam, granule, powder, tablet, and capsule. Furthermore, in order to use it for injection, it can be produced in the form of a freeze dried substance or a granulated substance that is to be dissolved in a physiological saline or a buffering solution (for example PBS) or the like immediately before use so as to prepare a medical fluid. Carrier included in the antimicrobial agent can be different according to the form of the antimicrobial agent. The process itself in which various forms of pharmaceuticals are prepared using materials including the antimicrobial. peptide (main component) and various carriers (secondary component) can be performed according to a conventionally known method, and this does not characterize the present invention so that the detailed description thereof will be omitted. As a detailed information source for prescription, for example, "Comprehensive Medicinal Chemistry" edited by Corwin Hansch and published by Pergamon Press (1990) can be referred to.

The antimicrobial agent described herein can be used by a method or a dose in accordance with the form and the purpose thereof. The antimicrobial peptide including Tau associated sequence described herein can maintain a high antimicrobial activity even in a condition where relatively high concentration of cation, saline (for example sodium chloride) or organic compound such as serum is present. Hence it is also preferable for the antimicrobial peptide described herein to be used in situations where cation, saline or serum is present. For example, the antimicrobial agent can be administered, as a liquid agent, intravenously, intramuscularly, subcutaneous, intracutaneous or intraperitoneal injection, or by enema to a patient.

Alternatively, the agent can be administered orally when it is in a solid form such as a tablet. When it is used for the purpose of sanitizing (sterilizing) the surface of sanitary ceramic ware or preventing decay of foods, a liquid agent containing a relatively large amount (e.g., 1 to 100 mg/ml) of peptide can be sprayed directly onto the surface of a targeted object, or the surface of a targeted object can be wiped with fabric or paper impregnated with the liquid agent. These are only examples, and the same form and usage as those of conventional peptide antibiotics, agricultural chemicals, medicines or the like having a peptide as a component can be applied. For example, for cancer patients that are subjected to radiotherapy or aids patients, prevention and treatment of bacterial infection are important concerns. The antimicrobial peptide described herein can exhibit high antimicrobial effect against bacteria responsible for infectious diseases (for example gram-positive bacteria such as *Staphylococcus aureus*). Therefore, the antimicrobial peptide of the present invention described herein is useful as a main component of an antimicrobial agent.

The polynucleotide encoding the antimicrobial peptide of the present invention can be used as a material for so-called gene therapy. For example, a gene (typically DNA segment, or RNA segment) encoding the antimicrobial peptide is incorporated into a suitable vector, and transduced into a targeted site, so that the antimicrobial peptide related to the present invention can be expressed constantly in an organism (cell). Therefore, the polynucleotide (DNA segment, RNA segment or the like) encoding the antimicrobial peptide of the present invention is useful as a pharmaceutical for preventing or treating bacterial infection to the above-described patients or the like.

It is important to prevent bacterial infection during culture of skin, bone or various organs in the field of regenerative medicine. The antimicrobial peptide described herein has a very low toxicity with respect to the mammal cells or tissues and can exhibit an antimicrobial effect selectively with respect to the bacterium. Therefore, this is very useful as a pharmaceutical for preventing bacterial infection of a cultured organ or the like. For example, as shown in the examples later, bacterial infection of an organ during culture can be prevented by adding solely the antimicrobial peptide or an antimicrobial agent having the peptide as one of the main components in an appropriate concentration in a culture solution.

Furthermore, with respect to cultured cells or cultured tissues, the polynucleotide encoding the antimicrobial peptide of the present invention can be used as a material used for gene therapy. For example, a gene (typically DNA segment, or RNA segment) encoding the antimicrobial peptide of the present invention is incorporated into a suitable vector, and transduced into a targeted cultured tissue, so that the antimicrobial peptide related to the present invention can be expressed constantly or in a desired period in a cultured tissue (or cell). Therefore, the polynucleotide (DNA segment, RNA segment or the like) encoding the antimicrobial peptide of the present invention is useful as a pharmaceutical for preventing or treating bacterial infection of cultured tissues.

Hereinafter, several examples of the present invention will be described, but they are not intended to limit the present invention.

Example 1

Synthesis of Peptides 15 types of peptide (samples 1 to 14, comparative sample 1) were produced with a peptide synthesis machine that will be described later. Table 1 shows the amino acid sequences of these synthetic peptides.

TABLE 1

| Sample No. | Amino Acid Sequence | Total Number of Amino Acid Residues |
|---|---|---|
| sample 1 | KKVAVVR (SEQ ID NO: 23) | 7 |
| sample 2 | KVQIINKK (SEQ ID NO: 24) | 8 |
| sample 3 | LKRKLQRVQIVYK (SEQ ID NO: 25) | 13 |
| sample 4 | LKRKLQRVQIINK (SEQ ID NO: 26) | 13 |
| sample 5 | KKVAVVRKKVAVVR (SEQ ID NO: 27) | 14 |
| sample 6 | KVQIINKKKVQIINKK (SEQ ID NO: 28) | 16 |
| sample 7 | RKKKRKVKKVAVVR (SEQ ID NO: 29) | 14 |
| sample 8 | KKVAVVRTKKVAVVRT (SEQ ID NO: 30) | 16 |
| sample 9 | RKKKRKVKVQIINKK (SEQ ID NO: 31) | 15 |
| sample 10 | RKKKRKVKKVAVVRT (SEQ ID NO: 32) | 15 |
| sample 11 | KVQIINKKLDVSNLMWWLL (SEQ ID NO: 33) | 19 |
| sample 12 | KVQIINKKLMWWLL (SEQ ID NO: 34) | 14 |
| sample 13 | PPRKKRTVVKVQIINKK (SEQ ID NO: 35) | 17 |
| sample 14 | VQIVYKVQIVYK (SEQ ID NO: 36) | 12 |
| comparative sample 1 | LPPLERLTLD (SEQ ID NO: 37) | 10 |

As illustrated in Table 1, samples 1 to 14 each includes a Tau associated sequence (underlined portions in Table 1).

The peptide in sample 1 (SEQ ID NO: 23) is a peptide composed of a Tau associated sequence (KKVAVVR) made up of 7 amino acid residues selected from the amino acid sequence in the aforementioned (d).

The peptide in sample 2 (SEQ ID NO: 24) is a peptide composed of a Tau associated sequence (KVQIINKK) made up of the amino acid sequence (8 amino acid residues) in the aforementioned (a).

The peptide in sample 3 (SEQ ID NO: 25) is a peptide composed of a Tau associated sequence (VQIVYK: SEQ ID NO: 39) made up of 6 amino acid residues selected from the amino acid sequence in the aforementioned (b) and a NLS associated sequence (LKRKLQR: SEQ ID NO: 13) made up of 7 amino acid residues arranged at the N-terminal of the Tau associated sequence.

The peptide in sample 4 (SEQ ID NO: 26) is a peptide composed of a Tau associated sequence (VQIINK: SEQ ID NO: 38) made up of 6 amino acid residues selected from the amino acid sequence in the aforementioned (a) and a NLS associated sequence (LKRKLQR: SEQ ID NO: 13) made up of 7 amino acid residues arranged at the N-terminal of the Tau associated sequence.

The peptide in sample 5 (SEQ ID NO: 27) is a peptide composed of Tau associated sequences (KKVAVVR) made up of 7 amino acid residues selected from the amino acid sequence in the aforementioned (d), and arranged in 2-units tandem.

The peptide in sample 6 (SEQ ID NO: 28) is a peptide composed of Tau associated sequences (KVQIINKK) made up of the amino acid sequence in the aforementioned (a), and arranged in 2-units tandem.

The peptide in sample 7 (SEQ ID NO: 29) is a peptide composed of a Tau associated sequence (KKVAVVR) made up of 7 amino acid residues selected from the amino acid sequence in the aforementioned (d) and a NLS associated sequence made up of 7 amino acid residues (specifically, a modified NLS: RKKKRKV in which the N-terminal proline of PKKKRKV shown in SEQ ID NO: 7 is substituted by Arginine) arranged at the N-terminal of the Tau associated sequence.

The peptide in sample 8 (SEQ ID NO: 30) is a peptide composed of Tau associated sequences (KKVAVVRT) made up of the amino acid sequence in the aforementioned (d), and arranged in 2-units tandem.

The peptide in sample 9 (SEQ ID NO: 31) is a peptide composed of a Tau associated sequence (KVQIINKK) made up of the amino acid sequence in the aforementioned (a) and a NLS associated sequence made up of 7 amino acid residues (specifically, the aforementioned modified NLS: RKKKRKV) arranged at the N-terminal of the Tau associated sequence.

The peptide in sample 10 (SEQ ID NO: 32) is a peptide composed of a Tau associated sequence (KKVAVVRT) made up of the amino acid sequence in the aforementioned. (d) and a NLS associated sequence made up of 7 amino acid residues (specifically, the aforementioned modified NLS: RKKKRKV) arranged at the N-terminal of the Tau associated sequence.

The peptide in sample 11 (SEQ ID NO: 33) is a peptide composed of a Tau associated sequence (KVQIINKK) made up of the amino acid sequence in the aforementioned (a), a linker-sequence portion (LDVSN) made up of 5 amino acid residues arranged at the C-terminal of the Tau associated sequence, and a LBS associated sequence made up of 6 amino acid residues arranged at the C-terminal of the linker portion. The "LD" at the N-terminal of the linker portion are also 2 amino acid residues link to the C-terminal of the amino acid sequence in the aforementioned (a) within an actual protein. Hence a sequence composed of these 10 amino acid residues (KVQI D) is equivalent to a sequence composed of 10 amino acid residues at the N-terminal of an inter-repeat domain (IR/R1-R2) exists between R1 and R2 of Tau protein.

The peptide in sample 12 (SEQ ID NO: 34) is a peptide composed of a Tau associated sequence (KVQIINKK) made up of the amino acid sequence in the aforementioned (a) and a LBS associated sequence (LMWWLL: SEQ ID NO: 15) made up of 6 amino acid residues arranged at the C-terminal of the Tau associated sequence.

The peptide in sample 13 (SEQ ID NO: 35) is a peptide composed of a Tau associated sequence (KVQIINKK) made up of the amino acid sequence in the aforementioned (a) and a NLS associated sequence (PPRKKRTVV: SEQ ID NO: 10) made up of 9 amino acid residues arranged at the N-terminal of the Tau associated sequence.

The peptide in sample 14 (SEQ ID NO: 36) is a peptide composed of Tau associated sequences (VQIVYK) made up of 6 amino acid residues selected from the amino acid sequence in the aforementioned (b), and arranged in 2-units tandem.

On the other hand, the peptide (LPPLERLTLD: SEQ ID NO: 37) of the comparative sample 1 is a completely unrelated synthesized peptide composed of 10 amino acid residues and does not include Tau associated sequence. Further, the carboxyl group of the C-terminal amino acid (—COOH) in all the samples is amidated (—CONH$_2$).

The above-described peptides (each includes 20 or less amino acid residue(s)) were synthesized by a solid synthesis method (Fmoc method) using a commercially available peptide synthesis machine (PEPTIDE SYNTHESIZER 9050 manufactured by PerSeptive Biosystems). As a condensing agent, HATU (Applied Biosystems product) was used, and the resin and the amino acids used in the solid synthesis method were purchased from NOVA biochem. To amidate the C-terminal of the amino acid sequence, "Rink Amide resin (100 to 200 mesh)" was used as the solid carrier.

Therefore, a peptide chain is elongated from Fmoc-amino acid that is bound to a resin by repeating deprotection reaction and condensation reaction according to the synthesis program of the above-described peptide synthesizing machine, so that a synthesized peptide of a targeted length was obtained. More specifically, Fmoc, which is an amino protecting group of an amino acid, is cleaved and removed with 20% piperidine/dimethylformamide (DMF) (peptide synthesis grade manufactured by KANTO KAGAKU), cleaned with DMF, reacted with 4 eq of Fmoc-amino acid (—OH) each, and cleaned with DMF. This operation was repeated. Then, after all the elongation reaction of the peptide chain was completed, the Fmoc group was cleaved with 20% piperidine/DMF, and the above-described reaction product was cleaned with DMF and methanol in this order.

After solid synthesis, the synthesized peptide chain and the resin were both transferred to a centrifuge tube, and 1.8 mL of ethanediol, 0.6 mL of m-cresol, 3.6 mL of thioanisole, and 24 mL of trifluoroacetic acid were added thereto, and then the mixture was stirred at room temperature for 2 hours. Thereafter, resin bound to the peptide chain was filtrated and removed. Then, cooled ethanol was added to the filtrate, and a peptide precipitate was obtained by cooling with iced water. Thereafter, the supernatant was discarded by centrifugation (for five minutes at 2500 rpm). Cool diethyl ether was again added to the precipitate and stirred sufficiently, and then centrifugation was performed in the same conditions as above. This process of stirring and centrifugation was repeated in total of three.

The obtained peptide precipitate was vacuum-dried and purified with a high speed liquid chromatography (Waters 600 manufactured by Waters Corp.).

More specifically, pre-column (Guard-Pak Delta-pak C18 A300 manufactured by Nippon Waters) and C18 reverse phase column (XTerra (registered trademark) column, MS C18, 5 μm, 4.6×150 mm manufactured by Nippon Waters) were used, and a mixed solution of 0.1% trifluoroacetic acid aqueous solution and 0.1% trifluoroacetic acid acetonitrile solution was used as an eluent. In other words, separation and purification were performed for 30 to 40 minutes using the above-described columns at a flow rate of 1.5 mL/min while increasing over time the amount of the trifluoroacetic acid acetonitrile solution contained in the eluent (providing the concentration gradient from 10% to 80% in volume ratio). The peptide eluted from the reverse phase column was detected at a wavelength of 220 nm using an ultraviolet ray detector (490E Detector manufactured by Waters) and shown on a recording chart as the peaks.

The molecular weight of each eluted peptide was determined, using Voyager DE RP (trademark) manufactured by PerSeptive Biosystems, based on MALDI-TOF MS (Matrix-Assisted Laser Desorption Time of Flight Mass Spectrometry). As a result, it was confirmed that the targeted peptide was synthesized and purified.

Example 2

Antimicrobial Activity of Synthesized Peptides (1)

Regarding the antimicrobial peptide in samples 1 to 14 and the comparative sample 1, the antimicrobial activities (minimum inhibitory concentration: MIC) with respect to gram-negative bacteria (*Escherichia coli*) and gram-positive bacteria (*Staphylococcus aureus*) were determined, as described below, by a liquid medium dilution technique using a 96-well microplate. First, a drug (synthesized peptide) solution having a concentration of 40 times of the highest test concentration was prepared using sterile distilled water, and thereafter liquid-bouillon mediums ("NUTRIENT BROTH Dehydrated" manufactured by DIFCO) having peptide concentrations of 200, 100, 50, 25, 12.5, 6.25, 3.13, 1.56 and 0.78 μM were produced respectively. The produced liquid-bouillon mediums including the peptide of each concentration were then fed to the 96-well microplate at 100 μL a time.

At the same time, test bacteria cultured for 18 hours at 37° C. on an agar plate ("Muller Hinton Agar" manufactured by DIFCO) were gathered by scratching with a loop, and then suspended in a sterilized physiological saline. Bacterial suspension 5 μL prepared at an equivalent of 2×10$^7$ cells/mL was respectively inoculated (number of bacteria to be tested: approximately 1×10$^6$ cells/mL) onto the above-described liquid-bouillon mediums including the peptide of each concentration and fed to each well of the above-described microplate. After inoculation, the microplate was then incubated in an incubator at 37° C., and the presence of bacteria was evaluated based on the turbidity 24 hours later. The minimum drug concentration (peptide concentration), in which an increased in turbidity caused by bacteria was not detected at the time of measurement, was defined as MIC (minimum inhibitory concentration) (unit: μM) in the present embodiment. The results are illustrated in Table 2.

TABLE 2

Antimicrobial Activities (MIC: μM)

| Sample No. | S. aureus | E. coli |
|---|---|---|
| Sample 1 | 50 | 200 |
| Sample 2 | 200 | 200 |
| Sample 3 | 3.13 | 6.25 |
| Sample 4 | 6.25 | 100 |
| Sample 5 | 12.5 | 100 |
| Sample 6 | 1.56 | 6.25 |
| Sample 7 | 3.13 | 6.25 |
| Sample 8 | 6.25 | 50 |
| Sample 9 | 0.78 | 3.13 |
| Sample 10 | 3.13 | 12.5 |
| Sample 11 | 12.5 | 25 |
| Sample 12 | 3.13 | 12.5 |
| Sample 13 | 0.78 | 3.13 |
| Sample 14 | 25 | 50 |
| Comparative Sample 1 | >200 | >200 |

As clearly illustrated in the results shown in Table 2, all antimicrobial peptides having Tau associated sequence (samples 1 to 14) exhibited excellent antimicrobial activities. Among these antimicrobial peptides, peptides having 2-units tandem Tau associated sequences (samples 5, 6, 8, 14), peptides having Tau associated sequence and NLS associated sequence (samples 3, 4, 7, 9, 10, 13) and peptides having Tau associated sequence and LBS associated sequence (samples 11, 12) exhibited particularly high antimicrobial activities against gram-positive bacteria (S. aureus). On the other hand, no antimicrobial activity were identified in the comparative peptide (comparative sample 1) composed of 10 amino acid residues.

Example 3

Antimicrobial Activity of Synthesized Peptides (2)

Next, the antimicrobial activities (MIC) against gram-positive bacteria (S. aureus) in the presence of serum and high concentration of cation were tested with the same method as Example 2. However, only the above-described sample 9 was used as the test peptide. Specifically, a drug (synthesized peptide of sample 9) solution having a concentration of 40 times of the highest test concentration was prepared using sterile distilled water. Thereafter, MHB mediums ("Mueller Hinton Broth" manufactured by DIFCO) including high concentration of cation with peptide concentrations of 50, 25, 12.5, 6.25, 3.13, 1.56 and 0.78 μM were produced respectively. The cation included was prepared as follows: dissolving 3.68 g of $CaCl_2 \cdot 2H_2O$ in 100 mL of purified water (10 mg.$Ca^{2+}$/mL), and thereafter adding 500 μL thereof into 100 mL of Mueller Hinton Broth; and dissolving 8.36 g of $MgCl_2 \cdot 6H_2O$ in 100 mL of purified water (10 mg.$Mg^{2+}$/mL), and thereafter adding 250 μL thereof into 100 mL of Mueller Hinton Broth.

Mediums (hereinafter "MHB serum mediums including high concentration of cation") were further prepared by adding horse serum (mechanically sterilized Nippon Biotest Laboratories inc. product), which made up of 10% volume ratio of the entire medium, into the MHB mediums including high concentration of cation. The MHB serum mediums including high concentration of cation had peptide concentrations of 50, 25, 12.5, 6.25, 3.13, 1.56 and 0.78 μM.

Next, the above-described MHB mediums including high concentration of cation and having peptide of each concentration, and the above-described MHB serum mediums including high concentration of cation and having peptide of each concentration were fed to the 96-well microplate at 100 μL a time, and the MIC were determined using the same method as example 2. As comparison, commercially available MHB mediums having peptide concentration of 50, 25, 12.5, 6.25, 3.13, 1.56 and 0.78 μM were used.

TABLE 3

Antimicrobial Activities (MIC: μM) against S. aureus

| | MHB | MHB + Cation | MHB + Cation + Horse Serum |
|---|---|---|---|
| Sample 9 | 3.13 | 3.13 | 3.13 |

As clearly illustrated in the results shown in Table 3, it had been verified that the peptide of the present invention could maintained a high antimicrobial activity even in the presence of high concentration of cation (in this example, peptide including high concentration of calcium and magnesium) and serum. Therefore, the antimicrobial peptide of the present invention is also preferred to be used in strains (for example, blood) in which a relatively high quantity of organic matter such as serum, and 1, 2 or more kinds of cation (or saline) are present.

Example 4

Hemolytic Activity of Synthesized Peptides

A test on the hemolytic activity of 2 kinds of synthesized peptides (sample 9 and sample 10) in example 1 was performed and served as indicator of the effects of these peptides on animal cell (erythrocyte). The hemolytic activity test in the present example was performed as follows. Specifically, sample peptides were dissolved in PBS (pH7.4), and thereafter 10 stages of twice diluted strains (sample solutions) with peptide concentration of 400, 200, 100, 50, 25, 12.5, 6.25, 3.13, 1.56 and 0.78 μM were prepared. Here, PBS was used as a control of 0% hemolysis, and PBS containing 0.1% of triton X-100 was used as a control of 100% hemolysis. Erythrocyte of fiber-free sheep's blood was then added to these sample solutions such that the volume ratio (v/v) was 1% of these sample solutions. After adding the above-described red blood cells, the sample solutions were incubated for 1 hour at 37° C., and thereafter the hemolysis was ceased with cold water. Next, centrifugal separation at 3000 rpm was performed for 4 hours at 4° C.

After centrifugal separation, each supernatant was fed to the 96-well microplate, and absorbency under 540 nm wavelength was determined. The hemolytic rate (%) was then calculated by the following formula based on the results determined: $\{(A_{exp}-A_0)/A_{100}\} \times 100$. Here, $A_{exp}$ represents the absorbency of the sample solutions supernatants, $A_o$ represents the absorbency of the control of 0% hemolysis, and $A_{100}$ represents the absorbency of the control of 100% hemolysis. The results are shown in Table 4. The hemolytic rate was considered as 0% in the case where the hemolytic rate was negative (%).

TABLE 4

| Peptide concentration (μM) | Hemolysis of sheep's erythrocytes (%: {($A_{exp}$-$A_0$)/$A_{100}$} × 100) | |
|---|---|---|
| | Sample 9 | Sample 10 |
| 6.25 | 1.5% | −2.2% |
| 3.13 | 0.1% | −0.8% |
| 1.56 | −3.7% | −2.1% |
| 0.78 | −2.2% | −2.1% |

As clearly illustrated in the results shown in Table 4, it had been verified that the hemolytic activities of the antimicrobial peptides described herein (sample 9 and sample 10) were significantly low, and the antimicrobial peptides (antimicrobial agents) were desirable to be applied to mammalian cells.

Example 5

Preparation of Granules

After 50 mg of peptide of the sample 9 were mixed with 50 mg of crystallized cellulose and 400 mg of lactose, 1 mL of a mixed solution of ethanol and water was added and the mixture was kneaded. This kneaded product was granulated according to a regular method, and thus a granule having the antimicrobial peptide as the main component was obtained.

Specific examples of the present invention have been described above, but they are only illustrative and not limiting the scope of the claims. All changes and

---

What is claimed is:

1. A method for producing an antimicrobial composition containing a peptide having an antimicrobial property against at least one kind of bacteria, the method comprising:
   synthesizing a peptide of 30 amino acids or less containing an amino acid sequence selected from the group consisting of SEQ ID NO: 25, SEQ ID NO: 26, SEQ ID NO: 28, SEQ ID NO: 31, SEQ ID NO: 33, SEQ ID NO: 34, SEQ ID NO: 35, and SEQ ID NO: 36; and
   mixing the synthesized peptide with a pharmaceutically acceptable carrier.

2. The method according to claim 1, wherein the total number of amino acid residues included in the synthesized peptide is 20 amino acids or less.

3. The method according to claim 1, wherein the synthesized peptide is composed of an amino acid sequence selected from the group consisting of SEQ ID NO: 25, SEQ ID NO: 26, SEQ ID NO: 28, SEQ ID NO: 31, SEQ ID NO: 33, SEQ ID NO: 34, SEQ ID NO: 35, and SEQ ID NO: 36.

* * * * *